United States Patent
Ragaglia et al.

(10) Patent No.: US 6,441,365 B1
(45) Date of Patent: Aug. 27, 2002

(54) PROCESS AND APPARATUS FOR ELEMENTAL ANALYSIS WITH OXYGEN CONTROL

(75) Inventors: Luigi Ragaglia, Cassina de' Pecchi; Giacinto Zilioli, Cernusco S/N, both of (IT)

(73) Assignee: Thermoquest Italia S.p.A., Rodano (IT)

( * ) Notice: Subject to any disclaimer, the term of this patent is extended or adjusted under 35 U.S.C. 154(b) by 0 days.

(21) Appl. No.: 09/562,159

(22) Filed: May 1, 2000

(30) Foreign Application Priority Data

Jul. 5, 1999 (IT) ......................... MI99A0997

(51) Int. Cl.[7] ................................ G01V 8/00
(52) U.S. Cl. .................... 250/222.2; 356/311
(58) Field of Search ............... 250/222.2, 282, 250/222.1, 221; 356/311

(56) References Cited

U.S. PATENT DOCUMENTS

| | | | |
|---|---|---|---|
| 4,525,328 A | 6/1985 | Bredeweg | |
| 5,012,052 A | * 4/1991 | Hayes | 250/288 |
| 5,401,468 A | 3/1995 | Patashnick et al. | |
| 6,227,842 B1 | * 5/2001 | Lemelson et al. | 431/12 |

FOREIGN PATENT DOCUMENTS

| | | |
|---|---|---|
| EP | 0544142 A | 6/1993 |
| EP | 0586969 A | 3/1994 |
| EP | 0940677 A | 9/1999 |
| WO | WO 8707721 A | 12/1987 |

\* cited by examiner

*Primary Examiner*—Robert H. Kim
*Assistant Examiner*—Hoon K. Song
(74) *Attorney, Agent, or Firm*—Gibbons, Del Deo, Dolan, Griffinger & Vecchione

(57) ABSTRACT

In elemental analysers with a valve control system of inert gas and oxygen supply, which opens the oxygen supply at preset moments, with regard to the introduction of the sample into the combustion reactor, the oxygen supply is controlled by the detection, over time, of at least one of the parameters, whose variation is determined by flash combustion in the combustion reactor, closing the oxygen supply depending on said state over time. The parameters are brightness, temperature and pressure in the combustion chamber and/or pressure upstream the combustion chamber.

12 Claims, 3 Drawing Sheets

PROCESS AND APPARATUS FOR ELEMENTAL ANALYSIS WITH OXYGEN CONTROL

BACKGROUND OF THE INVENTION

Field of the Invention

The present invention relates to a method and apparatus to perform the contents analysis of C, H, N and S. in samples, by their flash combustion in oxygen.

Apparatuses are known of the type mentioned and are called elemental analysers, basically consisting of a so-called combustion chamber kept at high temperature (around 900° C.) in which the sample to be analysed is introduced.

The chamber, normally flushed out by a flow of inert gas, is fed with oxygen to carry out said flash combustion, whose products are then sent to a reduction reactor and the chemical analysis apparatus.

It is very important, for analysis cost reasons and the maintenance of efficiency of the reduced copper which is present the reduction reactor, to provide an oxygen supply calibrated on the quantity actually necessary to carry out the sample combustion.

The collection of a certain amount of oxygen in a duct (loop) has already been suggested, to be sent to the combustion chamber after passing through the inert gas. Nevertheless, this preset amount must be chosen so as to guarantee the combustion of each sample type and weight hence, for samples requiring less oxygen or those of lesser weight, a part of the oxygen supplied is not involved in combustion and enters into the system downstream, oxidising the reducing layer and therefore causing an undue excessive copper consumption, as well as an undue excessive oxygen consumption.

To avoid this happening, the proposal has been made (Italian Patent Application No. M198A 000435 of 4/3/98) to supply oxygen directly through a valve system and to determine a priori the amount, taking into account the nature and weight of the sample to be analysed. This allows the exact measurement of the oxygen needed, but requires prior knowledge of the sample nature and also involves the presence of control software of lengthy and complex preparation.

It would be desirable to control the quantity of oxygen supplied each time, so as to correlate it to combustion needs (sample nature and quantity), setting aside knowledge of the sample characteristics and intervening to halt the oxygen supply each time when combustion is completed.

For the implementation of such a method, the parameter used to exercise influence over the time progression may consist of the brightness induced by the combustion in the combustion reactor, the temperature in the same combustion reactor or finally, the pressure in the combustion reactor, or upstream thereof, in the gas supply circuit.

BRIEF DESCRIPTION OF THE DRAWINGS

The various ways of implementing the method, according to the invention, are illustrated as follows with reference to the figures enclosed, in which.

DESCRIPTION OF THE PREFERRED EMBODIMENTS

Figure 1:
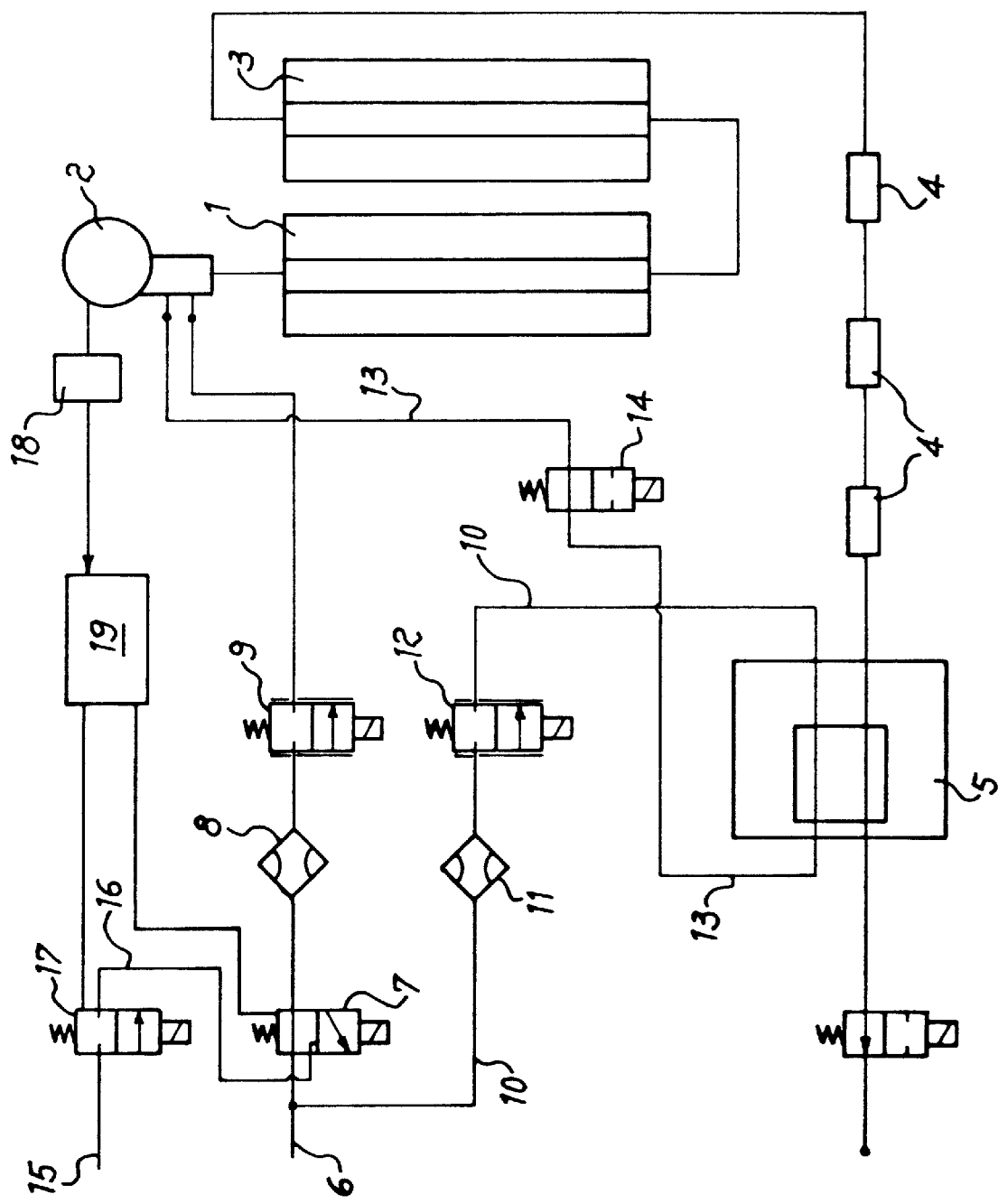
FIG. 1 is a diagram of an elemental analyser, in which the control of the oxygen supply is brought about on the basis of the brightness of the combustion reactor.

With reference to the figures, the general diagram of the apparatus comprises a combustion reactor 1, fed by a sample 2 and connected downstream to a reduction reactor 3, whose exit is connected to a series of filters 4 and consequently to a gas chromatographic column 5 with a relative detector, all being known per se.

At the pre-analysis stage a flow rate of inert gas (e.g. helium) coming from a source 6, is fed to sampler 2 and to the combustion reactor 1, said flow rate passes in sequence through a 3-way valve 7, a flow sensor 8 and a proportional valve 9, before reaching the sampler 2. Helium is also continuously fed through a line 10, a flow sensor 11 and a proportional valve 12, to the detector of the gas-chromatographic system, acting as reference line. When leaving the detector, the helium is sent through a line 13, with a valve 14, to the sampler washing 2.

A source of oxygen 15, on whose line of exit 16 is located a valve 17, also feeds the 3-way valve 7, whose the switching allows to send helium or oxygen alternatively, to the sampler and combustion reactor 1, according to the analysis moments.

In particular, upon commencement of each analysis, valves 17 and 7 are switched to send oxygen into combustion reactor 1. After a few seconds, the sampler 2 drops the sample into the reactor, already at a high temperature (around 900° C.), where combustion of the sample occurs in the presence of $O_2$. This combustion gives rise to various phenomena, with a consequent variation of corresponding parameters, in particular: brightness, temperature and gas pressure. The recording of variations over time of such parameters gives, as shown in the figure diagrams, control over the quantity of oxygen supplied, so as to not exceed that which is necessary for combustion, for the reasons mentioned initially, by the switching of valves 7 and 17 to return to pre-analysis conditions.

In particular, in FIG. 1 a photodetector 18 is provided, which is sensitive to the brightness inside the combustion reactor 1. This brightness increases in a continuous or pulsated manner during combustion, but always with a maximum final value. Appropriate setting of the photodetector 18 can operate, through the computerised apparatus control system 19, the switching of valves 7 and 17 at the most appropriate moment.

Figure 2:
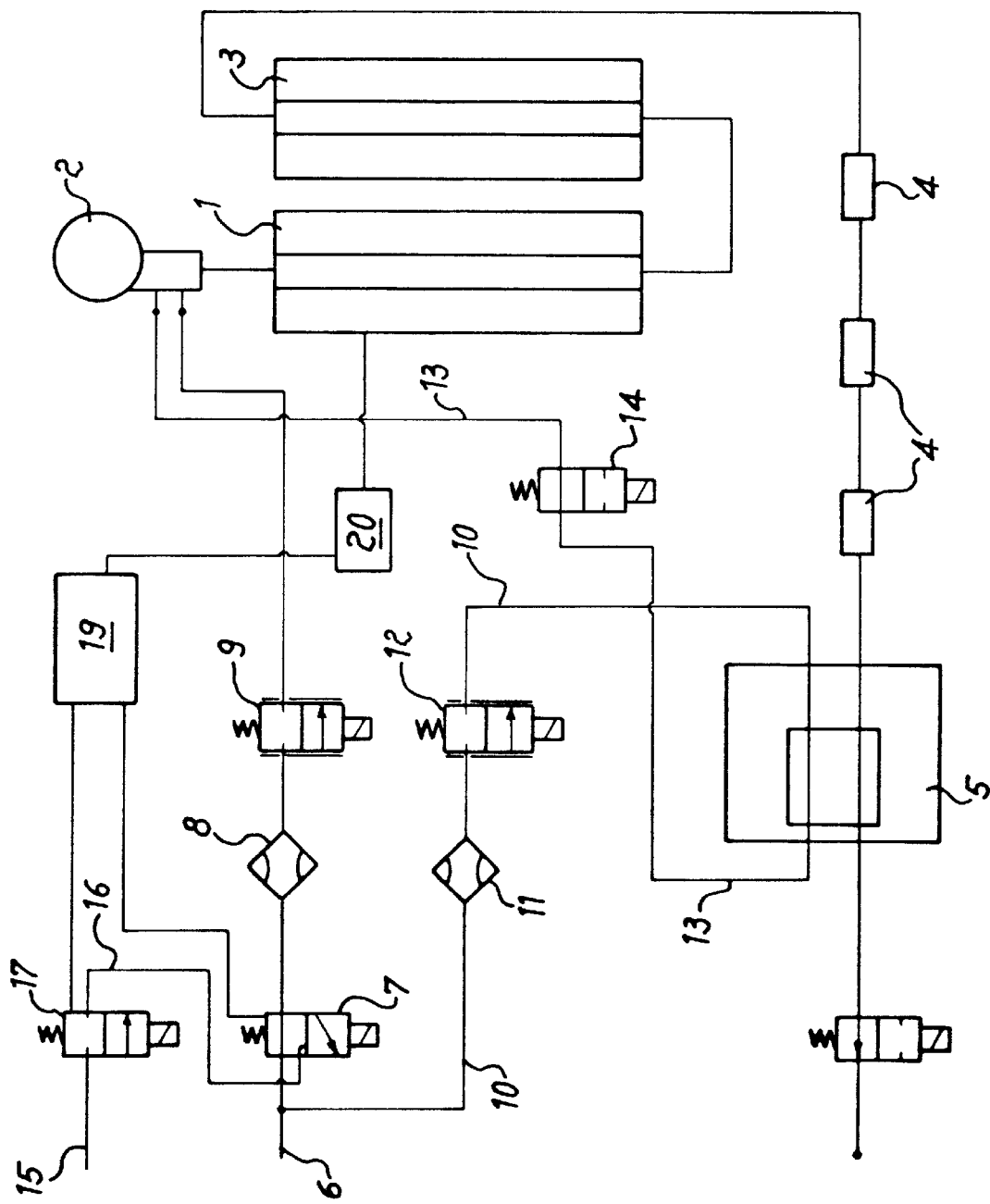
FIG. 2 is a diagram of an elemental analyser in which control of the oxygen supply is brought about on the basis of the temperature of the combustion reactor.

In place of, or in addition to the photodetector 18 it is possible to have a temperature sensor 20 (FIG. 2) inside the combustion reactor 1, which detects the temperature increase resulting from sample combustion and, in reaching the maximum value or at the beginning of the subsequent decrease acts in controlling, through computer 19, the switching of valves 7 and 17 to halt the oxygen supply.

Figure 3:
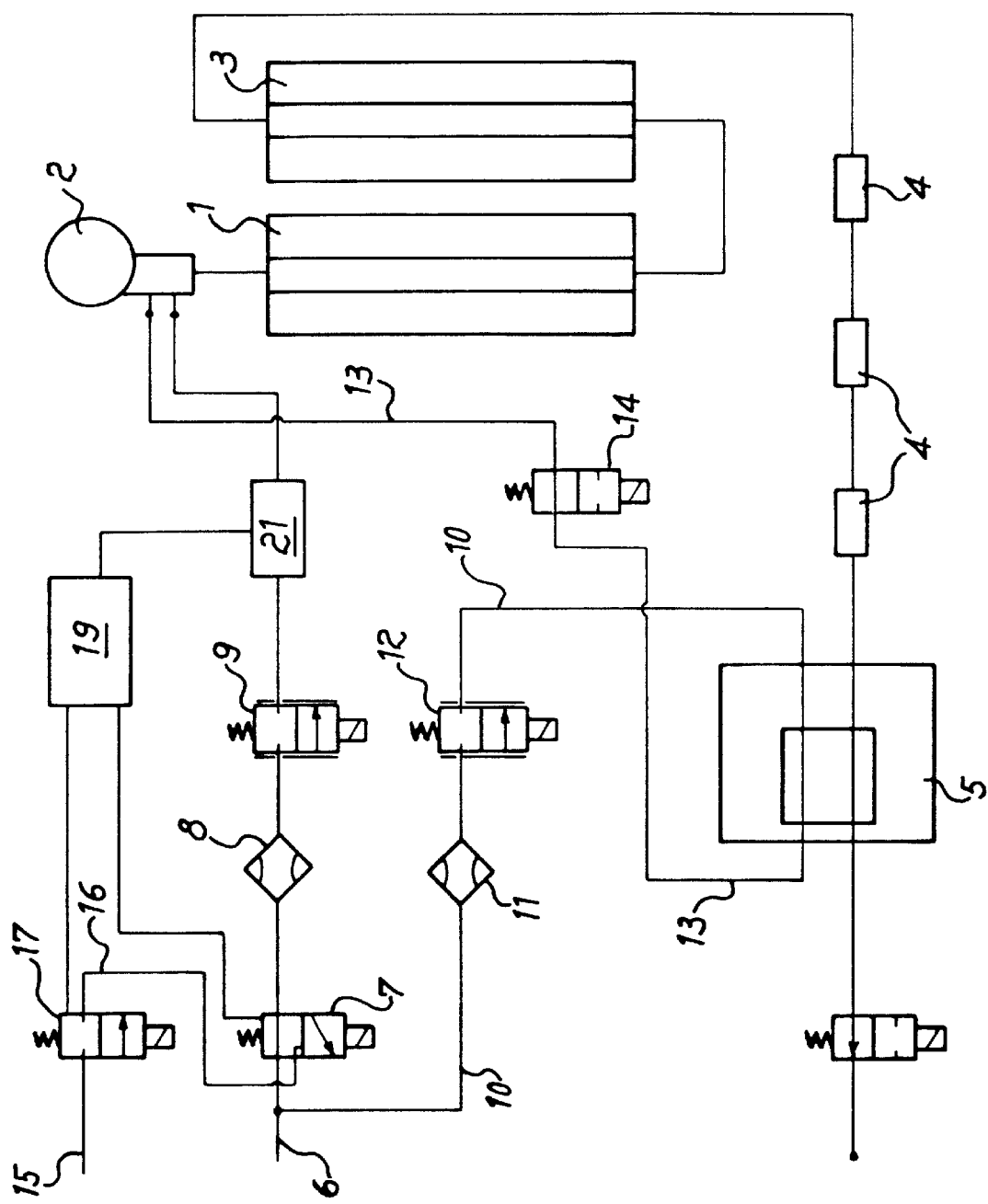
FIG. 3 is a diagram of an elemental analyser in which control of the oxygen supply is brought about on the basis of the pressure in the combustion reactor or immediately upstream thereof.

Finally, FIG. 3 shows the provision of an electronic digital device 21, that could be placed in the combustion reactor 1 or, as shown, immediately upstream thereof, in the gas supply line (helium or oxygen) to the same reactor.

It has been ascertained that, after the introduction of the sample into the reactor 1, the pressure starts to increase for several seconds, to then fall back to its initial value. During the decrease, at a certain point connected to the weight and nature of the sample introduced, the pressure increases again for a few seconds, to then fall back to its initial value once again. This rising point signals the end of sample combustion and the device, at the same moment in which it recognises this increase, switches valves 7 and 17 through computer 19, restoring the pre-analysis conditions.

This method achieves the desired measuring of the quantity of oxygen introduced, calibrated on that required for the complete combustion of the sample, without needing to resort to the pre-determination of this quantity, based on the nature and weight of the sample.

What is claimed is:

1. A method for controlling an oxygen supply in an elemental analyzer that has a combustion reactor and has a valve control system for supply of inert gas and oxygen, alternatively according to preset moments with respect to introduction of a sample to be combusted in the combustion reactor and analyzed in a chemical analyzer, charaterized by detecting over time a state of at least one of a plurality of parameters, whose variation is determined by a flash combustion in the combustion reactor, and by halting the oxygen supply, depending on the state over time, at a moment when combustion is completed.

2. A method according to claim 1, in which the parameter is brightness in the combustion chamber.

3. A method according to claim 1, in which the parameter is temperature in the combustion chamber.

4. A method according to claim 1, in which the parameter is pressure in the combustion chamber.

5. A method according to claim 1, in which the parameter is pressure upstream the combustion chamber.

6. A method according to any one of claim 1, characterized in that the oxygen supply is interrupted at or near return to initial values of the detected parameter, after a normal or abnormal increase in A values thereof.

7. A method according to claim 5, characterised in that the oxygen supply is interrupted during a second pressure increase, following a first increase and a reduction towards the initial value, which occur immediately after onset of combustion.

8. Apparatus for elemental analysis, comprising a combustion reactor, an alternative inert gas or oxygen supply circuit to the combustion reactor, a valve control system for supply of gases, a computer for the computerized checking of the apparatus, and a chemical analyzer, characterized in that the apparatus comprises at least one sensor to detect a state over time of at least one of a plurality of parameters altered by a flash combustion of a sample in the combustion reactor, and a means to switch, by way of said computer, the valve system from an oxygen supply condition to an inert gas supply condition, upon a pre-chosen parameter reaching a preset point or preset area in a curve representing the state over time, at a moment when combustion is completed.

9. Apparatus according to claim 8, characterised in that said sensor is a photodetector.

10. Apparatus according to claim 8, characterised in that said sensor is a temperature detector.

11. Apparatus according to claim 8, characterised in that said sensor is a pressure detector.

12. Apparatus according to claim 11, characterised in that said pressure detector is positioned upstream the combustion reactor, near the same, on the inert gas and oxygen supply line to A combustion reactor.

* * * * *